US008049078B2

(12) United States Patent
Berke

(10) Patent No.: US 8,049,078 B2
(45) Date of Patent: Nov. 1, 2011

(54) HABANERO PEPPER HYBRID PX11423487

(75) Inventor: Terry Berke, Zamora, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 573 days.

(21) Appl. No.: 12/201,234

(22) Filed: Aug. 29, 2008

(65) Prior Publication Data

US 2009/0064370 A1    Mar. 5, 2009

Related U.S. Application Data

(60) Provisional application No. 60/969,139, filed on Aug. 30, 2007.

(51) Int. Cl.
| | |
|---|---|
| *A01H 5/00* | (2006.01) |
| *A01H 5/08* | (2006.01) |
| *A01H 5/10* | (2006.01) |
| *C12N 5/04* | (2006.01) |
| *C12N 15/10* | (2006.01) |

(52) U.S. Cl. ............... 800/317.1; 800/265; 800/278; 435/6.1; 435/430.1

(58) Field of Classification Search .......... None
See application file for complete search history.

(56) References Cited

U.S. PATENT DOCUMENTS

| 5,262,316 A | 11/1993 | Engler et al. ............... 435/172.3 |
| 2007/0234441 A1* | 10/2007 | Allersma et al. ............. 800/280 |
| 2009/0064369 A1 | 3/2009 | Berke ....................... 800/317.1 |

OTHER PUBLICATIONS

Perkins, C. PI 639657 'Chocolate Scotch Bonnet' deposited 1995.*
Sugita et al. Breeding Science 54: 111-115 (2004).*
Boukema, I. Euphytica 29: 433-439 (1980).*
Anaya-Lopez et al. HortScience 38(2): 251-255 (2003).*
Berke, "Hybrid seed production in capsicum," *J. of New Seeds*, 1(3/4):49-67, 1999.
Chae et al., "Development of resistant pepper lines against anthracnose using interspecific crossing between *Capsicum baccaturm* and *C. annuum*," *Capsicum & Eggplant Newsletter*, 22:121-124, 2003.
Panda et al., "Cytomorphology of induced octoploid chili pepper (*Capsicum annuum* L.)," *Theor. Appl. Gene.*, 68(6):567-577, 1984.
Pickersgill, "Genetic resources and breeding of *Capsicum* ssp.," *Euphytica*, 96:129-133, 1997.
South African Certificate of Grant of a Plant Breeder's Right No. ZA 992183 for Pepper (*Capsicum* L.) Variety HOTAZEL, Jun. 12, 1999.

* cited by examiner

*Primary Examiner* — David T Fox
(74) *Attorney, Agent, or Firm* — SNR Denton US LLP; Alissa Eagle, Esq.

(57) ABSTRACT

The invention provides seed and plants of the habanero pepper line designated PX11423487. The invention thus relates to the plants, seeds and tissue cultures of habanero pepper hybrid PX11423487, and to methods for producing a habanero pepper plant produced by crossing a plant of pepper hybrid PX11423487 with itself or with another pepper plant, such as a plant of another line. The invention further relates to seeds and plants produced by such crossing. The invention further relates to parts of a plant of habanero pepper hybrid PX11423487, including the fruit and gametes of such plants.

20 Claims, No Drawings

HABANERO PEPPER HYBRID PX11423487

This application claims the priority of U.S. Provisional Appl. Ser. No. 60/969,139, filed Aug. 30, 2007, the entire disclosure of which is incorporated herein by reference.

BACKGROUND OF THE INVENTION

1. Field of the Invention

The present invention relates to the field of plant breeding and, more specifically, to the development of habanero pepper hybrid PX11423487.

2. Description of Related Art

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform lines requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop plant which has been subject to such breeding programs and is of particular value is the habanero pepper. Peppers are commonly broken down into three groupings: bell peppers, sweet peppers, and hot peppers. Most popular pepper varieties fall into one of these categories, or as a cross between them. However, these groupings are not absolute, as both "hot pepper" and "sweet pepper" encompass members belonging to several different species. Additionally members of each of the three groups may be different cultivars of the same species. For example, the bell pepper, the jalapeño pepper, and the "Thai sweet" all belong to the species *Capsicum annuum* L.

Hot pepper refers to both the fruit and the plant. Hot peppers are the smaller hotter types of chile peppers, which are the fruit of the plant *Capsicum* from the nightshade family, Solanaceae. The chile pepper originated in the Americas; however, today chile peppers are grown around the world. Primarily, they are used as spices and vegetables in cuisine. Hot peppers, including some inedible varieties, are also grown for ornamental and medicinal uses. While there are other pungent varieties of *C. annuum*, many well known hot peppers are members of different species. For example, both the cayenne pepper and the tabasco pepper are varieties of *Capsicum frutenscens*, while the hottest peppers, including the habanero and naga varieties, are members of *Capsicum chinense*.

The hot pepper fruit is eaten cooked or raw. Its fiery hot flavor is concentrated along the top of the pod. Capsaicin (8-methyl-N-vanillyl-6-nonenamide) is the main active ingredient along with several related chemicals—collectively called capsaicinoids, that give hot peppers their characteristically hot flavor. The stem end of the pod has glands which produce the capsaicin, which then flows down through the pod. The "heat" or pungency of chile peppers is measured in Scoville units. Bell peppers rank at zero Scoville units, jalapeños at 3,000-6,000, and habaneros at 300,000. Pure capsaicin has a reference value of 15,000,000 Scoville units.

*C. chinense* is usually cultivated as a herbaceous annual, although it can be grown as a perennial. The plant is typically bushy, has a densely branched stem, and grows to about 70 to 90 cm in height. The fruit is green when unripe, usually then changing to red or orange, but may turn brown, white, or pink. The fruit size varies, but is typically 2-5 centimeters in length at maturity. The species can grow in many climates; however, they thrive in warm and dry climates.

Habanero pepper breeding efforts have naturally focused on growing the hottest, most pungent line of peppers. The Red Savina Habanero at 577,000 Scoville units is among the hottest. However, some breeding programs have concentrated on retaining the flavor and aroma of the habanero pepper, while reducing the heat. Some lines with resistances to several pests and diseases are available. In the case of bell peppers, the development of molecular markers and a molecular linkage map for *C. annuum* has eased some of the problems associated with selecting simultaneously for multiple resistances and other desirable characteristics.

Tetraploidy and haploidy are relatively easy to induce in *Capsicum* species and an octaploid *Capsicum annuum* has been reported (Pandal et al., 1984). *Capsicum* species exhibit barriers to interspecific gene transfer. These include unilateral incompatibility, post-fertilization abortion, and nucleo-cytoplasmic interactions leading to male sterility or other abnormalities (Pickersgill and Barbara, 1997). However, the development of a pepper line resistant to the anthracnose fungal pathogen using interspecific crossing between *Capsicum baccatum* and *C. annuum* has been reported (Chae et al., 2003).

Hybrid vigor has also been documented in habanero peppers, and hybrids are gaining increasing popularity among farmers throughout the world, especially in countries with lower skilled labor costs (Berke, 1999).

While breeding efforts to date have provided a number of useful habanero pepper lines and varieties with beneficial traits, there remains a great need in the art for new varieties with further improved traits. Such plants would benefit farmers and consumers alike by improving crop yields and/or quality.

SUMMARY OF THE INVENTION

In one aspect, the present invention provides a hybrid habanero pepper plant designated PX11423487. Also provided are habanero pepper plants having all the physiological and morphological characteristics of the hybrid habanero pepper designated PX11423487. Parts of a habanero pepper plant according to the present invention are also provided, for example, including pollen, an ovule, a scion, a rootstock, a fruit, and a cell of the plant.

The present invention overcomes limitations in the prior art by providing, for example, seeds and plants of a habanero pepper variety having a combination of genes, the expression of which provides advantageous traits, such as resistance to Tobamovirus P0, and excellent tolerance to gemini viruses. The invention also concerns seed of habanero pepper hybrid PX11423487. The habanero pepper seed of the invention may be provided as an essentially homogeneous population of habanero pepper seed of the variety designated PX11423487. Essentially homogeneous populations of seed are generally free from substantial numbers of other seed. Therefore, seed of hybrid PX11423487 may be defined as forming at least about 97% of the total seed, including at least about 98%, 99% or more of the seed. The seed population may be separately grown to provide an essentially homogeneous population of habanero pepper plants designated PX11423487.

In another aspect of the invention, a plant of habanero pepper hybrid PX11423487 comprising an added heritable trait is provided. The heritable trait may comprise a genetic locus that is a dominant or recessive allele. In one embodiment of the invention, a plant of habanero pepper hybrid PX11423487 is defined as comprising a single locus conversion. In specific embodiments of the invention, an added genetic locus confers one or more traits such as, for example, herbicide tolerance, insect resistance, disease resistance, and modified carbohydrate metabolism. The trait may be, for example, conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In another aspect of the invention, a tissue culture of regenerable cells of a plant of hybrid PX11423487 is provided. The tissue culture will preferably be capable of regenerating plants capable of expressing all of the physiological and morphological characteristics of the variety, and of regenerating plants having substantially the same genotype as other plants of the variety. Examples of some of the physiological and morphological characteristics of the hybrid PX11423487 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides habanero pepper plants regenerated from a tissue culture of the invention, the plants having all the physiological and morphological characteristics of hybrid PX11423487.

In yet another aspect of the invention, processes are provided for producing habanero pepper seeds, plants and fruit, which processes generally comprise crossing a first parent pepper plant with a second parent pepper plant, wherein at least one of the first or second parent pepper plants is a plant of the variety designated PX11423487. These processes may be further exemplified as processes for preparing progeny habanero pepper seed or plants, wherein a first pepper plant is crossed with a second pepper plant of a different, distinct line to provide a progeny that has, as one of its parents, the pepper plant PX11423487. In these processes, crossing will result in the production of seed. The seed production occurs regardless of whether the seed is collected or not.

In one embodiment of the invention, the first step in "crossing" comprises planting seeds of a first and second parent pepper plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pepper plants into plants that bear flowers. A third step may comprise preventing self-pollination of the plants, such as by emasculating the male portions of flowers, (i.e., treating or manipulating the flowers to produce an emasculated parent pepper plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent pepper plants. Yet another step comprises harvesting the seeds from at least one of the parent pepper plants. The harvested seed can be grown to produce a habanero pepper plant or hybrid habanero pepper plant.

The present invention also provides the habanero pepper seeds and plants produced by a process that comprises crossing a first parent pepper plant with a second parent pepper plant, wherein at least one of the first or second parent pepper plants is a plant designated PX11423487. In one embodiment of the invention, habanero pepper seed and plants produced by the process are first generation progeny hybrid habanero pepper seed and plants produced by crossing a plant in accordance with the invention with another, distinct plant. The present invention further contemplates plant parts of a habanero pepper plant, and methods of use thereof. Therefore, certain exemplary embodiments of the invention provide progeny habanero pepper plant and seed thereof.

In still yet another aspect of the invention, the genetic complement of the habanero pepper plant hybrid designated PX11423487 is provided. The phrase "genetic complement" is used to refer to the aggregate of nucleotide sequences, the expression of which sequences defines the phenotype of, in the present case, a habanero pepper plant, or a cell or tissue of that plant. A genetic complement thus represents the genetic makeup of a cell, tissue or plant, and a hybrid genetic complement represents the genetic make up of a hybrid cell, tissue or plant. The invention thus provides habanero pepper plant cells that have a genetic complement in accordance with the habanero pepper plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid PX11423487 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by habanero pepper plant cells, tissues, plants, and seeds, formed by the combination of a haploid genetic complement of a pepper plant of the invention with a haploid genetic complement of a second pepper plant, preferably, another, distinct pepper plant. In another aspect, the present invention provides a habanero pepper plant regenerated from a tissue culture that comprises a hybrid genetic complement of this invention.

In still yet another aspect, the invention provides a plant of a hybrid habanero pepper that exhibits resistance to Tobamovirus P0, a greater (e.g., characterized as excellent) tolerance to gemini viruses compared to the O.P. variety "Habanero", about 16 days earlier maturity compared to "Habanero", and a high yield defined as about 2.5 times that of "Habanero", primarily due to a very high number of peppers per plant, wherein the expression of the traits are controlled by genetic means for the expression of the traits found in hybrid habanero pepper PX11423487.

In still yet another aspect, the invention provides a method of determining the genotype of a plant of habanero pepper hybrid PX11423487 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from hybrid PX11423487, the method comprising the steps of: (a) preparing a progeny plant derived from hybrid PX11423487, wherein said preparing comprises crossing a plant of the hybrid PX11423487 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid PX11423487. The plant derived from hybrid PX11423487 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid PX11423487 is obtained which possesses some of the desirable traits of the line as well as potentially other selected traits.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of habanero pepper hybrid PX11423487. This hybrid can be described as a typical habanero, with certain exceptional characteristics. The fruits are typically about 5.8 cm long×3.7 cm wide, with common habanero shape and smell. Immature color is a medium green, and fruits mature to a dull orange. Fruit pungency measured by HPLC using fruit grown in Woodland, Calif. during the summer 2005 growing season was about 214,720 Scoville Heat Units on a dry weight basis. It has high yield of about 765.5 grams per plant, mainly due to a high number of fruits per plant of about 72. Fruit weight was typically about 10.7 g per pepper, and plant height about 95 cm, with a semi-spreading plant habit. Hybrid PX11423487 generally matures to the ripe dull orange color in about 107 days after transplanting. PX11423487 is resistant to Tobamovirus P0, and exhibits excellent tolerance to gemini viruses. This variety shows uniformity and stability within the limits of environmental influence for the traits described hereinafter. Hybrid habanero pepper hybrid PX11423487 provides sufficient seed yield.

Hybrid PX11423487 exhibits a number of improved traits including extreme earliness, typically maturing in about 107 days after transplanting, which allows cultivation in certain areas that have been considered unfavorable for habanero growing such as Northern California. It exhibits excellent tolerance to gemini viruses which are found in the United States, but are also considered endemic to the primary habanero growing area: the Yucatan region. The development of the variety can be summarized as follows.

A. Origin and Breeding History of Habanero Pepper Hybrid PX11423487

The parents of Habanero pepper hybrid PX11423487 are pepper line HHA 114-1032 and HHA 114-1030. This variety was initially created by crossing HHA 114-1032 as a female parent to HHA 114-1030 as a male parent. Seeds were harvested from the female and the hybrid was first tested in Woodland, Calif. HHA 114-1032 is a uniform selection from the standard O.P. variety called 'Habanero.' HHA 114-1030, is a uniform selection from a Mexican landrace collected in 1993 from San Quentin, Mexico.

B. Physiological and Morphological Characteristics of Hybrid Habanero Pepper PX11423487

In accordance with one aspect of the present invention, there is provided a plant having the physiological and morphological characteristics of habanero pepper hybrid PX11423487. A description of the physiological and morphological characteristics of habanero pepper hybrid PX11423487 is presented in Table 1.

TABLE 1

Physiological and Morphological Characteristics of Hybrid PX11423487

| CHARACTERISTIC | Hybrid Habanero PX11423487 |
|---|---|
| 1. Type | Pepper |
| 2. Maturity | |
| Days From Transplanting Until Mature Green Stage | 92 |
| Days From Transplanting Until Mature Red Or Yellow Stage | 107 |
| Days From Direct Seeding Until Mature Green Stage | 122 |
| Days From Direct Seeding Until Mature Red Or Yellow Stage | 137 |
| 3. Plant | |
| Habit | Spreading |
| Attitude | Semi-erect |
| Height | 95.0 cm |
| Width | 80.0 cm |
| Length Of Stem From Cotyledons To First Flower | 20.0 cm |
| Length Of Third Internode (From Soil Surface) | 15.0 cm |
| Basal Branches | Many (more than 3) |
| Branch Flexibility | Willowy (Cayenne Long Red) |
| Stem Strength (Breakage Resistance) | Intermediate |
| 4. Leaves | |

TABLE 1-continued

Physiological and Morphological Characteristics of Hybrid PX11423487

| CHARACTERISTIC | Hybrid Habanero PX11423487 |
|---|---|
| Width | 70.0 mm |
| Length | 85.0 mm |
| Petiole Length | 28.0 mm |
| Mature Leaf Shape | Elliptic |
| Leaf Color | Medium Green |
| Leaf And Stem Pubescence | Absent (Yolo Wonder L) |
| Margin Undulation | Medium |
| Blistering | Weak |
| 5. Flowers | |
| Number Of Flowers Per Leaf | 2 |
| Number Of Calyx Lobes | 5 |
| Number Of Petals | 5 |
| Flower Diameter | 17.0 mm |
| Corolla Color | White |
| Corolla Throat Markings | None |
| Anther Color | Yellow |
| Style Length | Same as stamen |
| Self-Incompatibility | Absent |
| 6. Fruit | |
| Group | Bell (Yolo Wonder L) Ancho (Mexican Chili) |
| Immature Fruit Color | Medium Green (Long Thin Cayenne) |
| Mature Fruit Color | Orange |
| Pungency | Hot (Jalapeno) |
| Capsaicin Per Gram Dry Fruit | 13.4 mg |
| Scoville Units (Dry Fruit) | 214,700 |
| Flavor | Strong Pepper Flavor |
| Fruit Glossiness | Dull |
| Surface Smoothness | Rough (Long Thin Cayenne) |
| Fruit Position | Pendent (Jalapeno) |
| Calyx Shape | Saucer-shaped (Flat, Non-enveloping) |
| Calyx Diameter | 16.0 mm |
| Length | 58.0 mm |
| Diameter At Calyx Attachment | 37.0 mm |
| Diameter At Mid-Point | 38.0 mm |
| Flesh Thickness At Mid-Point | 2.5 mm |
| Average Number Of Fruits Per Plant | 72 |
| Large Fruits | 8% (weight range 13-16 g) |
| Medium Fruits | 81% (weight range 9-12 g) |
| Small Fruits | 11% (3-8 g) |
| Average Fruit Weight | 10.7 gm |
| Fruit Base-Shape | Rounded (Jalapeno) |
| Fruit Apex Shape | Pointed (Long Thin Cayenne) |
| Fruit Shape | Acorn |
| Fruit Shape (Longitudinal Section) | Heart-shape |
| Fruit Shape (Cross-Section, At Level Of Placenta) | Quadrangular |
| Fruit Set | Concentrated |
| Interloculary Grooves | Medium |
| Fruits With One Locule | 0% |
| Fruits With Two Locules | 5% |
| Fruits With Three Locules | 85% |
| Fruits With Four Locules | 10% |
| Fruits With Five Or More Locules | 0% |
| Average Number Of Locules | 3.2 |
| Pedicel Length | 23.0 mm |
| Pedicel Thickness | 3.8 mm |
| Pedicel Shape | Curved |
| Pedicel Cavity | Absent |
| Depth Of Pedicel Cavity | 0 mm |
| 7. Seed | |
| Cavity Length | 46.0 mm |
| Cavity Diameter | 31.0 mm |
| Placenta Length | 23.5 mm |
| Number Of Seeds Per Fruit | 75 |
| Per 1000 Seeds | 4.6 gm |
| Color | Yellow |
| 8. Anthocyanin | |
| Seeding Hypocotyl | Weak |
| Stem | Weak |
| Node | Weak |
| Leaf | Absent |
| Pedicel | Absent |
| Calyx | Absent |
| Fruit | Absent |
| 9. Disease Resistance (rate from 1 (most susceptible) to 9 (most resistant) | |
| Cucumber Mosaic Virus | 3 |
| Pepper Mottle Virus | 3 |
| Potato Y Virus | 3 |
| Tobacco Etch Virus | 3 |
| Tobacco Mosaic Virus | 9 |
| 10. Other Diseases And Insects | |
| *Phytophthora* Root Rot (*Phytophthora Capsici*) | 3 |
| Other (TSWV) | 1 |
| Other (Gemini Virus) | 6 |

*These are typical values. Values may vary due to environment. Other values that are substantially equivalent are also within the scope of the invention.

C. Breeding Habanero Pepper Hybrid PX11423487

One aspect of the current invention concerns methods for crossing the habanero pepper hybrid PX11423487 with itself or a second plant and the seeds and plants produced by such methods. These methods can be used to produce progeny habanero pepper seeds and the plants grown therefrom. Hybrid seeds can also be produced by crossing the parent lines of hybrid PX11423487.

The development of new varieties using one or more starting varieties is well known in the art. In accordance with the invention, novel varieties may be created by crossing hybrid PX11423487 followed by multiple generations of breeding according to such well known methods. New varieties may be created by crossing with any second plant, or with itself. In selecting such a second plant or progeny plant to cross for the purpose of developing novel varieties, it may be desired to choose those plants which either themselves exhibit one or more selected desirable characteristics or which exhibit the desired characteristic(s) in further progeny. Once initial crosses have been made, inbreeding and selection take place to produce new varieties. For development of a uniform line, often five or more generations of selfing and selection are involved.

Backcrossing can also be used to improve an inbred plant, including a parent of a hybrid. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. When selecting a second plant to cross with PX11423487 for the purpose of developing novel habanero pepper lines, it will typically be preferred to choose those plants which either themselves exhibit one or more selected desirable characteristics or which exhibit the desired characteristic(s) when in hybrid combination. Examples of desirable traits of habanero peppers include: seed yield, germination, seedling vigor, maturity, fruit yield, ease of fruit setting, disease tolerance and adaptability for soil and climate conditions. Consumer-driven traits, such as preference for a given fruit size, shape, color, texture, and taste— especially "hotness" or pungency (capsaicinoid content) are other traits that can be incorporated into new lines of habanero pepper plants developed by this invention.

One of the more desirable traits that may be provided by this invention is improved resistance to different viral, fungal, and bacterial pathogens. Anthracnose and Phytophthora blight are fungal diseases affecting various species of pepper. Fruit lesions and fruit rot are the commercially most important aspects of these diseases. Bacterial leaf spot and Cercospora leaf spot are other diseases affecting pepper plants, especially during the wet season. Viral pathogens affecting pepper plants include the tomato spotted wilt virus, cucumber mosaic virus, tobacco mosaic virus, and some Geminiviridae (gemini viruses) which are circular, single stranded, DNA plant viruses Improved resistance to insect pests is another desirable trait that may be incorporated into new lines of habanero pepper plants developed by this invention. Insect pests affecting the various species of pepper include the Pepper weevil, aphids, whitefly, leafhoppers and flea beetles. Peppers are also affected by root-knot nematodes.

D. Performance Characteristics

As described above, hybrid PX11423487 exhibits desirable agronomic traits, including resistance to Tobamovirus P0, and excellent tolerance to gemini viruses, a yield of about 765.5 g/plant, each plant bearing about 72 fruit per plant, and extreme earliness, maturing about 107 days after transplanting. One important aspect of the invention thus provides seed of the variety for commercial use. Performance characteristics of the line were the subject of an objective analysis of the performance traits of the line relative to other lines. The results of the analysis are presented below.

TABLE 2

Performance Characteristics For Hybrid PX11423487

| Variety | Color at maturity | Maturity (DAT) | Yield g/plt | Length cm | Width cm | Avg. Wt. g/fruit | % dry matter | Scoville HU dry basis |
|---|---|---|---|---|---|---|---|---|
| Habanero | orange | 126 | 154.0 | 5.0 | 3.5 | 11.1 | 12.2 | 258,876 |
| PX11423487 | orange | 107 | 765.5 | 5.8 | 3.7 | 10.7 | 12.2 | 214,727 |
| Caribbean Red | red | 133 | 40 | 5 | 3.2 | 8.0 | 11.3 | 364,832 |

As shown above, hybrid PX11423487 exhibits superior yield of about 765.5 g per plant, each plant commonly bearing about 72 fruit per plant. In comparison, competing variety Caribbean Red generally yields about 5 fruit weighing a total of about 40 g, per plant. The standard variety 'Habanero' generally yields about 14 fruit weighing a total of about 154 g per plant. The fruit of hybrid PX11423487 is longer and slightly wider than most competing varieties. Hybrid PX11423487 also matures very quickly, as shown above, generally maturing about 107 days after transplanting compared to 126 for Habanero and 133 for Caribbean Red.

E. Further Embodiments of the Invention

When the term habanero pepper hybrid PX11423487 is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those habanero pepper plants which are developed by a plant breeding technique called backcrossing, wherein essentially all of the desired morphological and physiological characteristics of a variety are recovered in addition to the single locus transferred into the variety via the backcrossing technique. This specifically includes the modification of a parent line of a hybrid variety, as such modifications will be passed to hybrids produced therefrom.

Backcrossing methods can be used with the present invention to improve or introduce a characteristic into the present variety. The parental pepper plant which contributes the locus for the desired characteristic is termed the nonrecurrent or donor parent. This terminology refers to the fact that the nonrecurrent parent is used one time in the backcross protocol and therefore does not recur. The parental pepper plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a habanero pepper plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, the progeny of a cross between progeny habanero pepper plants of a backcross in which a parent of PX11423487 is a recurrent parent comprise (i) the desired trait from the non-recurrent parent and (ii) all of the physiological and morphological characteristics of the parent of PX11423487 as determined at the 5% significance level when grown in the same environmental conditions, and the other parent of PX11423487.

Habanero pepper varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of habanero pepper plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of habanero pepper are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Pepper Hybrid PX11423487 by Genetic Engineering

Many useful traits that can be introduced by backcrossing, as well as directly into a plant, are those which are introduced by genetic transformation techniques. Genetic transformation may therefore be used to insert a selected transgene into the pepper line of the invention or may, alternatively, be used for the preparation of transgenes which can be introduced by backcrossing. Methods for the transformation of plants, including pepper, are well known to those of skill in the art. Techniques which may be employed for the genetic transformation of pepper include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

*Agrobacterium*-mediated transformation of pepper explant material and regeneration of whole transformed pepper plants (including tetraploids) from the transformed shoots has been shown to be an efficient transformation method (U.S. Pat. No. 5,262,316).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pepper lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Octaploid: A cell or organism having eight sets of chromosomes.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a pepper variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a pepper plant by transformation.

Triploid: A cell or organism having three sets of chromosomes.

H. Deposit Information

A deposit of habanero pepper hybrid PX11423487, disclosed above and recited in the claims, has been made with the American Type Culture Collection (ATCC), 10801 University Blvd., Manassas, Va. 20110-2209. The date of deposit was Aug. 31, 2007. Upon issuance of a patent, all restrictions upon the deposit will be removed, and the deposit is intended to meet all of the requirements of 37 C.F.R. §1.801-1.809. The accession number for those deposited seeds of habanero pepper hybrid PX11423487 is ATCC Accession No. PTA-8622. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,262,316
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., Plant Physiol., 88:547, 1988.
Berke, J. New Seeds, 1:3-4, 1999.
Bird et al., Biotech. Gen. Engin. Rev., 9:207, 1991.
Bustos et al., Plant Cell, 1:839, 1989.
Callis et al., Plant Physiol., 88:965, 1988.
Chae et al., Capsicum Eggplant Newsltr., 22:121-124, 2003.
Choi et al., Plant Cell Rep., 13: 344-348, 1994.
Dekeyser et al., Plant Cell, 2:591, 1990.
Ellul et al., Theor. Appl. Genet., 107:462-469, 2003.
EP 534 858
Fraley et al., Bio/Technology, 3:629-635, 1985.
Fromm et al., Nature, 312:791-793, 1986.
Fromm et al., Plant Cell, 1:977, 1989.
Gibson and Shillito, Mol. Biotech., 7:125, 1997
Klee et al., Bio-Technology, 3(7):637-642, 1985.
Kuhlemeier et al., Plant Cell, 1:471, 1989.
Marcotte et al., Nature, 335:454, 1988.
Marcotte et al., Plant Cell, 1:969, 1989.
Midwest Veg. Prod. Guide for Commercial Growers (ID:56), 2003
Odel et al., Nature, 313:810, 1985.
Omirulleh et al., Plant Mol. Biol., 21(3):415-428, 1993.
Pandal et al., Theor. Appl. Gene., 68(6):567-577, 1984.
Pickersgill and Barbara, Euphytica, 96(1):129-133, 1997
Potrykus et al., Mol. Gen. Genet., 199:183-188, 1985.
Roshal et al., EMBO J., 6:1155, 1987.
Schaffner and Sheen, Plant Cell, 3:997, 1991.
Schemthaner et al., EMBO J., 7:1249, 1988.
Siebertz et al., Plant Cell, 1:961, 1989.
Simpson et al., EMBO J., 4:2723, 1985.
Terada and Shimamoto, Mol. Gen. Genet., 220:389, 1990.
Uchimiya et al., Mol. Gen. Genet., 204:204, 1986.
Wang et al., Science, 280:1077-1082, 1998.
Williams et al., Nucleic Acids Res., 18:6531-6535, 1990.
WO 99/31248

What is claimed is:

1. A habanero pepper plant of habanero pepper hybrid variety PX11423487, a sample of seed of said variety having been deposited under ATCC Accession Number PTA-8622.

2. A plant that expresses all of the physiological and morphological characteristics of the plant of claim 1.

3. A seed that produces the plant of claim 1.

4. A seed that produces the plant of claim 2.

5. A plant part of the plant of claim 1.

6. The plant part of claim 5, wherein said part is selected from the group consisting of a fruit, pollen, rootstock, scion, an ovule and a cell.

7. A tissue culture of regenerable cells of the plant of claim 1.

8. The tissue culture according to claim 7, comprising cells or protoplasts from a plant part selected from the group consisting of embryos, meristems, cotyledons, pollen, leaves, anthers, roots, root tips, pistil, flower, seed and stalks.

9. A pepper plant regenerated from the tissue culture of claim 7, wherein the regenerated plant expresses all of the physiological and morphological characteristics of habanero pepper hybrid PX11423487, a sample of seed of said habanero pepper hybrid having been deposited under ATCC Accession Number PTA-8622.

10. A method of producing pepper seed, comprising crossing the plant of claim 1 with itself or a second pepper plant.

11. The method of claim 10, wherein a plant of habanero pepper hybrid PX11423487 is used as a female parent.

12. A method for producing a seed of a habanero pepper hybrid PX11423487-derived pepper plant comprising the steps of:
   (a) crossing a pepper plant of habanero pepper hybrid PX11423487, a sample of seed of said habanero pepper hybrid having been deposited under ATCC Accession Number PTA-8622, with a second pepper plant; and
   (b) allowing seed of a habanero pepper hybrid PX11423487-derived pepper plant to form.

13. The method of claim 12, further comprising the steps of:
   (c) crossing a plant grown from said habanero pepper hybrid PX11423487-derived pepper seed with itself or a second pepper plant to yield additional habanero pepper hybrid PX11423487-derived pepper seed;
   (d) growing said additional habanero pepper hybrid PX11423487-derived pepper seed of step (c) to yield additional habanero pepper hybrid PX11423487-derived pepper plants; and
   (e) repeating the crossing and growing steps of (c) and (d) to generate further habanero pepper hybrid PX11423487-derived pepper plants.

14. A method of vegetatively propagating a plant of habanero pepper hybrid PX11423487 comprising the steps of:
   (a) collecting tissue capable of being propagated from a plant of habanero pepper hybrid PX11423487, a sample of seed of said habanero pepper hybrid having been deposited under ATCC Accession Number PTA-8622;
   (b) cultivating said tissue to obtain proliferated shoots; and
   (c) rooting said proliferated shoots to obtain rooted plantlets.

15. The method of claim 14, further comprising growing plants from said rooted plantlets.

16. A method of introducing a desired trait into habanero pepper hybrid PX11423487 comprising introducing a transgene conferring the trait into a plant of habanero pepper hybrid PX11423487, a sample of seed of said habanero pepper hybrid having been deposited under ATCC Accession Number PTA-8622.

17. A pepper plant produced by the method of claim 16.

18. A method of determining the genotype of the plant of claim 1, comprising obtaining a sample of nucleic acids from said plant and detecting in said nucleic acids a plurality of polymorphisms.

19. The method of claim 18, further comprising the step of storing the results of the step of detecting the plurality of polymorphisms on a computer readable medium.

20. A method of producing peppers comprising:
   (a) obtaining the plant of claim 1, wherein the plant has been cultivated to maturity; and
   (b) collecting peppers from the plant.

\* \* \* \* \*